United States Patent
Brewer et al.

[11] 3,997,323
[45] Dec. 14, 1976

[54] HERBICIDAL METHOD EMPLOYING SUBSTITUTED DITHIN TETROXIDES

[75] Inventors: Arthur D. Brewer, Guelph, Canada; Robert W. Neidermyer, Cheshire, Conn.; William S. McIntire, Senatobia, Miss.

[73] Assignees: Uniroyal Inc., New York, N.Y.; Uniroyal, Ltd., Canada

[22] Filed: May 12, 1975

[21] Appl. No.: 576,485

Related U.S. Application Data

[62] Division of Ser. No. 357,757, May 7, 1973, Pat. No. 3,920,438.

[52] U.S. Cl. .................................. 71/91; 71/66; 71/67
[51] Int. Cl.[2] ............................................. A01N 9/12
[58] Field of Search .................................. 71/91, 90

[56] References Cited
UNITED STATES PATENTS

| | | | |
|---|---|---|---|
| 3,066,149 | 11/1962 | Slezak et al. | 71/91 |
| 3,299,098 | 1/1967 | Reifschneider | 71/91 |
| 3,439,051 | 4/1969 | Levine | 260/652.5 |
| 3,663,543 | 5/1972 | Gulbenk et al. | 71/90 |

OTHER PUBLICATIONS

Bottini, et al., "2–Methyl–5,6–Dihydro–1,4–etc.," (1966), CA64, p. 15890 (1966).
Asinger, et al. I, "Joint Action of Elementary Sulfur, etc.," (1971), CA76, No. 72466y, (1972).
Rubenstein, et al., "Preparation of Substituted, etc.," (1969), CA71, No. 91403p, (1969).
Asinger, et al. II, "Concomitant Action of Elementary, etc.," (1964), CA61, pp. 1854–1856, (1964).

*Primary Examiner*—Glennon H. Hollrah
*Attorney, Agent, or Firm*—James J. Long

[57] ABSTRACT

Regulation of the growth of plant life, including herbicidal, defoliant or desiccant effects, may be accomplished with certain 2,3-dihydro-1,4-dithiin 1,1,4,4-tetroxides of the formula

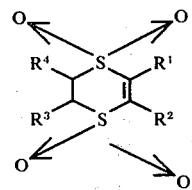

wherein the R's have various values such as hydrogen, alkyl, etc. Certain of the compounds, such as 2,3-dihydro-5,6-dimethyl-1,4-dithiin 1,1,4,4-tetroxide, are new chemicals, and are useful as pre-and post-emergent herbicides, and in harvest aid procedures, such as defoliation/desiccation of various crops, including cotton and potatoes.

27 Claims, No Drawings

HERBICIDAL METHOD EMPLOYING SUBSTITUTED DITHIN TETROXIDES

This is a division of application Ser. No. 357,757 filed May 7, 1973 now U.S. Pat. No. 3,920,438, issued Nov. 18, 1975.

This invention relates to a method of regulating the growth of plant life, including herbicidal, defoliant or desiccant affects, using certain 2,3-dihydro-1,4-dithiin 1,1,4,4-tetroxides, some of which are new chemical compounds.

Regulation of the growth of plant life is frequently desirable for a number of reasons. For example, the control of weeds is of great economic importance. Weed competition inhibits the production of foliage, fruit or seed of agricultural crops. The presence of weeds may also reduce the quality of the harvested crop and reduce harvesting efficiency. Weed control is essential for maximum production of many agronomic and horticultural crops including corn (*Zea mays* L.), rice (*Oryza sativah* L.) and soybeans (*Glycine max* (L.) Merr.). Weeds on non cropped areas may cause a fire hazard, undesirable drifting of sand or snow, irritation to persons with allergies and impaired beauty of the landscape. Aquatic weeds impede the flow of water and the progress of watercraft in canals and recreational waterways. Algae are unsightly and cause unpleasant odors in recreational waters as well as water reservoirs. Thus, suppression of undesirable weed and algae growth would have many advantages.

The invention, in one aspect, is based on the discovery that certain 2,3-dihydro-1,4-dithiin 1,1,4,4-tetroxide are remarkably effective preemergence and postemergence herbicides, aquatic herbicides and algicides.

Another form of regulation of plant growth that is of great economic importance is represented by the use of harvest aid chemical compounds. Harvest aid includes such procedures as desiccation and defoliation of crop leaves, desiccation of vines, regrowth control of certain crops such as cotton, the forcing of maturity of certain crops and abscission of fruit.

It will be understood that many crops growing under optimum conditions do not mature uniformly or soon enough to facilitate mechanical harvesting. Crops such as cotton, potatoes and sunflowers frequently require either desiccation or defoliation of foliage before harvesting can be accomplished. By defoliating cotton, mechanical pickers can be utilized more efficiently because of three factors. One, the leaves do not interfere with the actual picking process; two, leaves do not cause excess trash accumulation or staining of fiber; and three, the top bolls mature, allowing a "once through the field" type of harvest. Cotton defoliation with organic chemicals is a common practice and is described in U.S. Pat. Nos. 2,955,803, Goyette, Oct. 11, 1960; and 2,965,467, Markley, Dec. 20, 1960. In one important aspect, the invention provides chemical compounds which not only defoliate cotton leaves but also aid in stopping regrowth of leaves. Regrowth stains the fibers green, which reduces quality, and may require another defoliant application.

Potato vines need to be killed in order to facilitate mechanical digging. By desiccating the leaves and vines, the tuber skins mature and are less susceptible to scarring by the digger. Sunflower is mechanically harvested, but to obtain top yields, the stalk must be free of leaves. This defoliation also ripens the seed uniformly and conditions the head for easy plucking. Many type of fruit such as citrus must be pre-conditioned for abscission if mechanical harvesting is desired. Citrus is picked mechanically by shaking the tree. Without an abscission or loosening agent the fruit will not fall uniformly, requiring excessive, potentially damaging tree shaking. This invention provides certain new 2,3-dihydro-1,4-dithiin 1,1,4,4-tetroxides which are remarkably useful as harvesting aids in the foregoing respects, because of their ability to desiccate, defoliate, or cause abscission.

The chemical compounds useful in regulating growth of plant life in accordance with the invention are 2,3-dihydro-1,4-dithiin 1,1,4,4-tetroxides of the formula

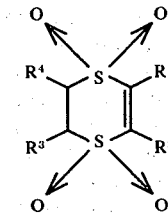

wherein $R^1$, $R^2$, $R^3$ and $R^4$ are selected from the group consisting of hydrogen and lower alkyl having one to two carbon atoms or an adjacent pair of R's are connected together in the form of a chain of three to four methylene groups, not more than two of the R's being hydrogen. Representative sets of values of the R's in such chemicals are as follows:

| $R^1$ | $R^2$ | $R^3$ | $R^4$ |
|---|---|---|---|
| $CH_3$ | $CH_3$ | H | H |
| $C_2H_5$ | $CH_3$ | H | H |
| $CH_3$ | $CH_3$ | H | $CH_3$ |
| | $-(CH_2)_4-$ | $CH_3$ | H |
| | $-(CH_2)_3-$ | $CH_3$ | H |
| $CH_3$ | $CH_3$ | $C_2H_5$ | H |
| $CH_3$ | $CH_3$ | $CH_3$ | $CH_3$ |
| $C_2H_5$ | H | $CH_3$ | $CH_3$ |
| | $-(CH_2)_4-$ | $CH_3$ | $CH_3$ |
| $C_2H_5$ | $CH_3$ | $CH_3$ | H |
| $C_2H_5$ | $CH_3$ | H | $CH_3$ |
| $CH_3$ | H | H | $CH_3$ |
| H | $CH_3$ | H | $CH_3$ |
| $C_2H_5$ | H | $CH_3$ | H |
| $C_2H_5$ | H | H | $CH_3$ |
| $CH_3$ | H | H | $C_2H_5$ |
| $CH_3$ | H | $C_2H_5$ | H |
| $C_2H_5$ | H | H | $C_2H_5$ |
| $C_2H_5$ | H | $C_2H_5$ | H |
| $CH_3$ | $CH_3$ | $-(CH_2)_4-$ | |
| $C_2H_5$ | H | $-(CH_2)_4-$ | |
| | $-(CH_2)_4-$ | H | H |

Chemicals of the foregoing class include: 2,3-dihydro-5,6-dimethyl-1,4-dithiin 1,1,4,4-tetroxide; 2-ethyl-5,6-dihydro-3-methyl-1,4-dithiin 1,1,4,4-tetroxide; 2,3-dihydro-2,5,6-trimethyl-1,4-dithiin 1,1,4,4-tetroxide; 5,6,7,8-tetrahydro-2-methyl-1,4-benzodithian 1,1,4,4-tetroxide; 2,3,6,7-tetrahydro-2-methyl-5H-cyclopenta-1,4-dithiin 1,1,4,4-tetroxide; 2-ethyl-2,3-dihydro-5,6-dimethyl-1,4-dithiin 1,1,4,4-tetroxide; 2,3-dihydro-2,3,5,6-tetramethyl-1,4-dithiin 1,1,4,4-tetroxide; 2-ethyl-5,6-dihydro-5,6-dimethyl-1,4-dithiin 1,1,4,4-tetroxide; 5,6,7,8-tetrahydro-2,3-dimethyl-1,4-benzodithian 1,1,4,4-tetroxide; 2-ethyl-5,6-dihydro-3,5-dimethyl-1,4-dithiin 1,1,4,4-tetroxide; 2-ethyl-5,6-dihydro-3,6-dimethyl-1,4-dithiin 1,1,4,4-tetroxide; 2,3-dihydro-2,5-dimethyl-1,4-dithiin 1,1,4,4-tetroxide; 2,3- dihydro-2,6-dimethyl-1,4-dithiin 1,1,4,4-tetroxide; 2-ethyl-5,6-dihydro-5-methyl-1,4-dithiin 1,1,4,4-tetroxide; 2-ethyl-5,6-dihydro-6-methyl-1,4-dithiin 1,1,4,4-tetroxide; 2-ethyl-2,3-dihydro-5-methyl-1,4-dithiin 1,1,4,4-tetroxide; 2-ethyl-2,3-dihydro-6-methyl-1,4-dithiin 1,1,4,4-tetroxide; 2,5-diethyl-2,3-dihydro-1,4-dithiin 1,1,4,4-tetroxide; 2,6-diethyl-2,3-dihydro-1,4-dithiin 1,1,4,4-tetroxide; 4a,5,6,7,8,8a-heahydro-2,3-dimethyl-1,4-benzOdithiin 1,1,4,4-tetroxide; 2-ethyl-4a,5,6,7,8,8a:hexahydro-1,4-benzodithiin 1,1,4,4-tetroxide; and 5,6,7,8-tetrahydro-1,4-benzodithian 1,1,4,4-tetroxide.

From the standpoint of herbicidal action, the invention contemplates application of any of the foregoing compounds, in herbicidally effective amount, to a locus where herbicidal effects are desired.

Certain of the foregoing compounds are especially useful as harvesting aids where effects such as defoliation, desiccation, abscission, or prevention of regrowth are desired, namely: 2,3-dihydro-5,6-dimethyl-1,4-dithiin 1,1,4,4-tetroxide; 2-ethyl-5,6-dihydro-3-methyl-1,4-dithiin 1,1,4,4-tetroxide; 2,3-dihydro-2,5,6,-trimethyl-1,4-dithiin 1,1,4,4-tetroxide; 5,6,7,8-tetrahydro-2-methyl-1,4-benzodithian 1,1,4,4-tetroxide; 2,3,6,7-tetrahydro-2-methyl-5H-cyclopenta-1,4-dithiin 1,1,4,4-tetroxide; 2-ethyl-2,3-dihydro-5,6-dimethyl-1,4-dithiin 1,1,4,4-tetroxide; 2,3-dihydro-2,3,5,6-tetramethyl-1,4-dithiin 1,1,4,4-tetroxide; 2-ethyl-5,6-dihydro-5,6-dimethyl-1,4-dithiin 1,1,4,4-tetroxide; 5,6,7,8-tetrahydro-2,3,-dimethyl-1,4-benzodithian 1,1,4,4-tetroxide; 2-ethyl-5,6-dihydro-3,5-dimethyl-1,4-dithiin 1,1,4,4-tetroxide; and 2-ethyl-5,6-dihydro-3,6-dimethyl-1,4-dithiin 1,1,4,4-tetroxide.

In one aspect, the invention is directed to new chemicals, useful in the regulation of plant growth, represented by the compounds having the structural formula stated above, wherein $R^1$, $R^2$, $R^3$, and $R^4$ are as stated above, provided further that when two of the R's are connected together, not more than one remaining R is hydrogen. The preferred new chemicals are those useful as harvest aids as described above.

German Pat. No. 1,957,860, Deutsche Gold und Silber Scheidenstalt, May 27, 1961, sets forth the structural formulas

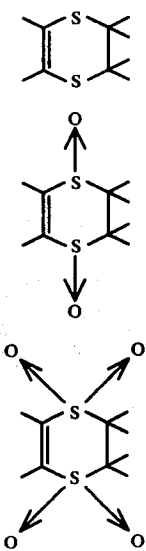

but does not disclose the present chemicals, nor is any plant growth regulating activity disclosed.

L. Levine, in a paper given at an American Chemical Society Meeting in San Francisco, 1968 (p. P024) disclosed the following

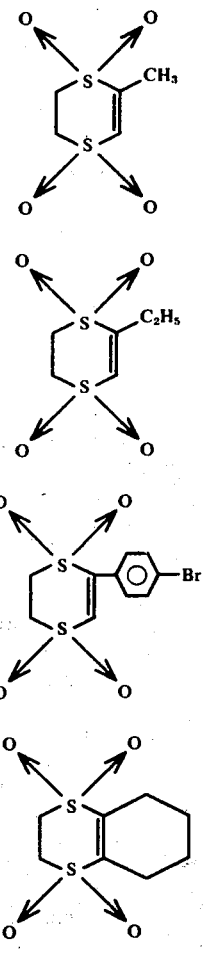

but did not disclose any plant growth regulating activity for the chemicals. The chemical of last formula is used as a herbicide in this invention; the other formulas represent compounds which are not active plant growth regulants.

Related chemicals have been reported in such references as: Henry et al. JACS 71, 2271 (1949); Parham et al. JACS 75, 1647 (1953); Parham et al. JACS 76, 1068 (1954); Parham et al. JACS 77, 1169 (1955); and Massingill et al. J. Org. Chem. 35, 823 (1970). None of the chemicals shown in those references has the surprising and unexpected utility found in the present chemicals.

The 2,3-dihydro-1,4-dithiin 1,1,4,4-tetroxides with which the invention is concerned may be made, for example, either by oxidation of the corresponding dithiin (I) or by oxidative decarboxylation of dithiin carboxylic acids (II)

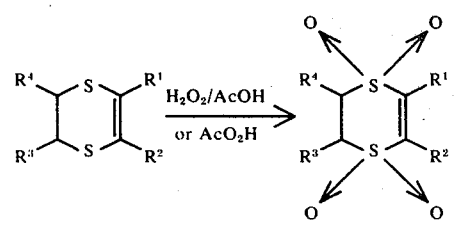

I

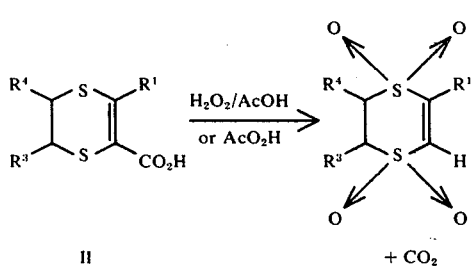

II     + CO₂ where the R's have the values set forth above.

Dithiims and dithiin acids may be prepared, for example, by two broad methods.

i. Reaction of an alpha-halocarbonyl compound such as an alpha-haloketone (III), or of an alpha-halo-beta-ketoester (IV), with a 1,2-dithiol (V), either in a basic followed by an acid medium, or in an acid medium throughout.

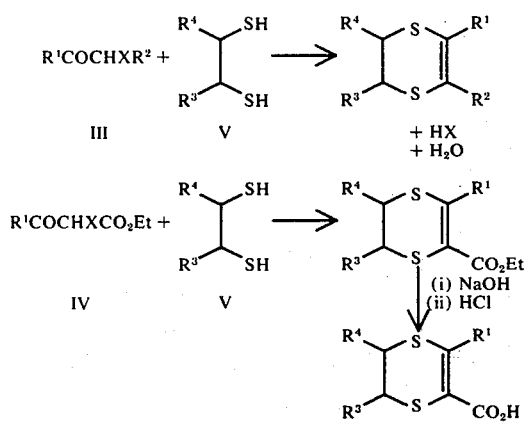

ii. Reaction of a 1,2-dithiol (III), with a ketone or aldehyde (VI) having an alpha-methylene group, or with a beta-ketoester (VII), followed by halogenation and ring expansion of the dithiolane (VIII) so produced.

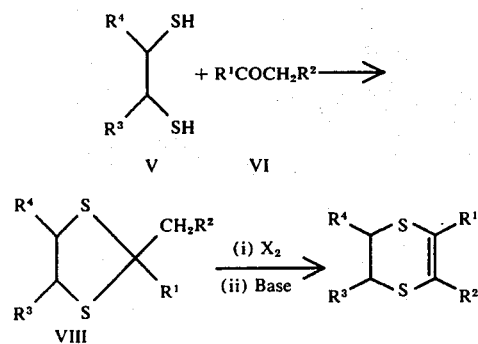

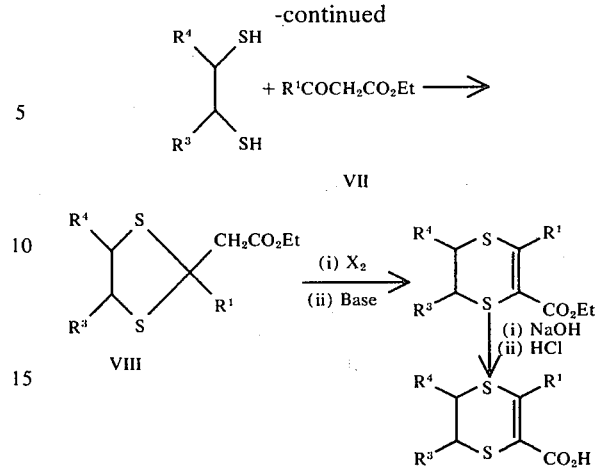

In certain cases the method of preparation employed may lead to a mixture of two different isomers of a particular chemical. Such an isomeric mixture may be used directly, if desired, for plant growth regulating purposes in accordance with the invention. Resolution of the mixture into products richer in one or the other of the isomers may be undertaken but is not necessary. Also, if desired, individual isomers may be prepared separately by a suitable synthetic method, and employed as plant growth regulants as described below.

To use the present chemicals as plant growth regulants, the chemicals is applied to a locus where such control is to be effected (i.e., either to the plant life itself and/or to the soil in which the plant is growing or to be grown), in an amount effective to regulate the growth of the plant in the manner desired. The amount employed follows conventional practice for such uses as herbicidal use or plant harvesting aid use (e.g., desiccation, defoliation, abscission of fruit, forcing of maturity; also control of regrowth), and the chemical is suitably applied as a formulation in accordance with conventional agricultural chemical practice.

Thus, the chemical may be impregnated on finely-divided or granular inorganic or organic carriers such as attapulgite clay, sand, vermiculite, corn cobs, activated carbon or other granular carriers known to the art. The impregnated granules may then be spread on the soil. Furthermore, the chemical may be formulated, for example, as a wettable powder by grinding it into a fine powder and mixing it with an inactive powdered carrier to which a surface active dispersing agent has been added. Typical powdered solid carriers are the various mineral silicates, e.g., mica, talc, pyrophyllite, and clays. The wettable powder may then be dispersed in water and sprayed on weeds, or the soil surface, or plants to be prepared for harvesting. Similarly, an emulsifiable concentrate may be prepared by dissolving the chemical in a solvent such as benzene, toluene, or other aliphatic or aromatic hydrocarbon to which a surface active dispersing agent has been added. The emulsifiable concentrate may then be dispersed in water and applied by spraying. The chemical may also be dissolved in water (for example, up to a concentration of 3000 ppm [parts per million]) and mixed with a surface active agent before spraying. Water solubility may be increased using a cosolvent system involving acetone, dimethyl sulfoxide or other water miscible solvents. Suitable surface active agents are well known to those skilled in the art, and reference may be had to McCutcheon's Detergents and Emulsifiers, 1970, Allured Publishing Corp., Ridgewood, N.J., or Hoffman et al. U.S. Pat. Nos. 2,614,916, cols. 2 to 4 and 2,547,724, cols. 3 and 4, for examples of appropriate surface active agents.

The concentration of active chemical in the formulation may vary widely, e.g., from 1 to 95%. The concentration of active chemical in dispersions applied to the soil or foliage is almost invariably from 0.002% to 75%. The chemical may also be dissolved in water at a concentration of, for example, 0.1 ppm to 2000 ppm for use as an algicide.

For use as a preemergence herbicide the chemical is frequently applied at rates of 0.05 to 25 pounds per acre to soil which contains weed and crop seed (either to the surface of the soil or incorporated into the upper one to three inches of soil). As a postemergence herbicide, the chemical is typically applied at rates of 0.05 to 40 pounds per acre to the foliage of weeds. The chemicals may be employed individually, or as a mixture of two or more chemicals.

For use as a harvesting aid, the chemical is typically employed at a concentration of from 0.005% to about 25% by weight, and applied at a rate usually equivalent to approximately 0.1 pound to 10 pounds per acre. Ordinarily the chemical is applied to the plants at least two days before harvesting. The chemicals indicated previously are not only remarkable for their ability to desiccate and/or defoliate the plants, and to cause abscission of fruit and to force maturity, but in addition make possible highly effective control of regrowth (e.g., 95% control or more). The chemicals may be employed individually, or as mixtures of two or more of the chemicals.

The most suitable rate of application in any given case may depend on such factors as soil type, soil pH, soil organic matter content, the quantity and intensity of rainfall before and after treatment, the air and soil temperature, light intensity and light duration per day. All of these factors can have an influence on the efficacy of the chemicals for a given plant growth control use.

The herbicidal use may include control of vegetation at industrial sites or selective weed control in crops such as corn, soybeans, carrots or rice.

Among the crops on which new chemicals of the invention are useful, particularly as harvesting aids, may be mentioned cotton (including the exceedingly difficult to defoliate California cotton), potatoes, sunflower, citrus, sugarbeets, sugarcane, peppers, milo, pineapple, tomatoes, grapes, and other crops such as are mentioned in U.S. Pat. No. 3,689,246, Young, Sept. 5, 1972.

The results obtained in accordance with the invention are particularly surprising in view of the fact that the precursors of the described chemicals, that is, the corresponding unoxidized analogs themselves, are not active herbicides or harvest aid chemicals.

The following examples will serve to illustrate the practice of the invention in more detail.

EXAMPLE 1 a. 3-Chloro-2-butanone (106.5 g, 1 mole) was added over a period of 3 hours to a stirred, externally cooled (0°) solution of ethanedithiol (94 g, 1 mole) and p-toluene sulfonic acid (0.5 g). The mixture was stirred at 0° for about 6 hours, then left overnight. Aqueous hydrochloric acid (17 mls) was separarted. The mixture was dissolved in benzene (500 ml), and heated under reflux with water removal by means of a Dean-Stark trap; a further 2 ml water collected (total 19 ml, calc. 18 ml). The benzene was removed in vacuo to give a clear liquid which was distilled at reduced pressure to give 2,3-dihydro-5,6-dimethyl-1,4-dithiin as a colorless or slightly green liquid, bp 72°–74°/0.7 mm (lit.) [J. L. Massingill et al., J.A.C.S. 35, 823 (1970)] 112°–113°/25 mm ) yield 114 g. (78%). NMR (nuclear magnetic resonance) 1.86 (6s), 3.12 (4s) (CDCl$_3$). IR (infra red), 2910 (shoulder); 1610, 1410 (sh); 1285 (sh); 1155 (sh); 1065, 865 (sh); 755 (sh).

b. 2,3-Dihydro-5,6-dimethyl-1,4-dithiin (146 g., 1 mole), dissolved in glacial acetic acid (100 cc), was added dropwise to a refluxing solution of 35% hydrogen peroxide (250 cc) and glacial acetic acid (250 cc). There is an exothermic reaction. When addition was complete, the solution was refluxed a further five minutes. On cooling, long white needles appeared. These were collected and recrystallized from boiling water to give 2,3-dihydro-5,6-dimethyl-1,4-dithiin 1,1,4,4-tetroxide as long white needles, mp 166°–168°, yield 166 g. (79%). NMR (CDCl$_3$) 2.13 (6s), 3.93 (4s). Anal. Calcd. for $C_6H_{10}O_4S_2$: C, 34.29; H, 4.86. Found: C, 34.25, 34.30; H, 4.81, 4.74. IR, 2980, 2940, 1550, 1400, 1300, 1180, 1100, 760.

EXAMPLE 2 a. The procedure of Example 1(a) is followed using 2-bromo-3-pentanone and ethanedithiol to give a 2 ethyl-5,6-dihydro-3-methyl-1,4-dithiin as a colorless oil, bp 88°–92°/2.8 mm, yield 41%. NMR, 1.04 (3t), 1.88 (3s), 2.19 (2q), 3.12 (4s). IR, 2920 (sh); 1600, 1410 (sh); 1285 (sh), 1155 (sh); 1065, 865 (sh); 755 (sh).

b. The procedure of Example 1(b) is followed to give 2-ethyl-5,6-dihydro-3-methyl-1,4-dithiin 1,1,4,4-tetroxide as white needles, mp 109°–113°, Yield 59%. Anal. Calcd. for $C_7H_{12}O_4S_2$: C, 37.50; H, 5.40. Found: C, 37.82, 38.17; H, 5.28, 5.44. NMR, 1.24 (3t), 2.16 (3s), 2.55 (2q), 3.88 (4s) (CDCl$_3$). IR, 2990, 2940, 1615, 1395, 1295, 1175, 1110, 765.

EXAMPLE 3 a. The procedure of Example 1(a) is repeated, using 1,2-propanedithiol and 3-chloro-2-butanone to give 2,3-dihydro-2,5,6-trimethyl-1,4-dithiin as a clear green liquid, bp 49.5°–51°/0.7 mm, yield 36.5% NMR 1.36 (3d), 1.88 (6s), 2.4–3.6 (3m) (CDCl$_3$). IR, 2905 (sh); 1605, 1410 (broad); 1250, 1155 (sh); 1065 (br); 730, 705.

b. The procedure of Example 1(b) is followed, giving 2,3-dihydro-2,5,6-trimethyl-1,4-dithiin 1,1,4,4-tetroxide as white needles mp 115°–116°, yield 49%. Anal. Calcd. for $C_7H_{12}O_4S_2$: C, 37.50; H, 5.40. Found: C, 37.28, 37.78; H, 5.95, 5.29. IR, 2975, 2950, 1545, 1400, 1290, 1180, 1100, 755.

EXAMPLE 4 a. The procedure of Example 1(a) is followed using 2-chloro-cyclohexanone and 1,2-propanedithiol to give 5,6,7,8-tetrahydro-2-methyl-1,4-benzodithian as a greenish oil, bp 127°–130°/2.3 mm, Yield 66%. NMR, 1.36 (3d), 1.4–1.88 (4m), 1.88–2.3 (4m), 2.6–3.7 (3m). IR, 2920, 1615, 1410, 1325, 1250, 1120, 855, 715.

b. The procedure of Example 1(b) is followed to give 5,6,7,8-tetrahydro-2-methyl-1,4-benzodithian 1,1,4,4-tetroxide as white needles, mp 158.5°–159.5°, Yield 61%. Anal. Calcd. for $C_9H_{14}O_4S_2$: C, 43.20; H, 560. Found: C, 43.26; H, 5.50. NMR, 1.57 (3d), 1.5–2.2 (4m), 2.3–3.0 (4m), 3.35–4.5 (3m), (CDCl$_3$). IR, 2965, 2920, 1625, 1305, 1130, 880, 770, 695.

EXAMPLE 5 a. The procedure of Example 1(a) is followed using 2-bromocyclopentanone and 1,2-propanedithiol to give 2,3,6,7-tetrahydro-2-methyl-5H-cyclopenta-1,4-dithiin as a greenish oil, bp 92.5°–93°/1 mm, Yield 69%. NMR, 1.42 (3d), 1.6–2.2 (2m), 2.2–2.65 (4m), 2.5–3.7 (3m) (CDCl$_3$) IR 2920, 1605, 1420, 1310, 1260, 1125, 870, 720.

b. The procedure of Example 1(b) is followed to give 2,3,6,7-tetrahydro-2-methyl-5H-cyclopenta-1,4-dithiin 1,1,4,4-tetroxide as white crystals, mp 158°–161°, Yield 64%. Anal. Calcd. for $C_8H_{12}O_4S_2$: C, 40.68; H, 5.12. Found: C, 41.23, 40.65; H, 5.16. NMR, 1.45 (3d) 1.8–2.4 (2m), 2.92 (4t), 3.75–4.35 (3m) (DMSO). IR, 1610, 1310, 1240, 1190, 1130, 900, 780, 690.

EXAMPLE 6 a. The procedure of Example 1(a) is repeated, using 1,2-butanedithiol and 3-chloro-2-butanone to give 2-ethyl-2,3-dihydro-5,6-dimethyl-1,4-dithiin as a colorless oil, bp 68°–81°/0.7, yield 35%, NMR 1.01 (3t), 1.4–2.9 (2m), 1.87 (6s), 2.6–3.4 (3m). IR, 2910 (sh), 1610 (sh); 1410, 1220 (sh); 1155 (sh); 1070, 735, 700.

b. The procedure of Example 1(b) is repeated, giving 2-ethyl-2,3-dihydro-5,6-dimethyl-1,4-dithiin 1,1,4,4-tetroxide as white needles, mp 103°–105°, yield 68%. NMR 1.16 (3t), 1.5–2.7 (2m), 1.65 (6s), 3.4–4.0 (3m). IR, 2970, 2940, 1630, 1400, 1295, 1180, 1120, 750. Anal. Calcd. for $C_8H_{14}O_4S_2$: C, 40.34; H, 5.92. Found: C, 40.35, 40.05; H, 5.83, 5.71.

EXAMPLE 7 a. The procedure of Example 1(a) is followed using 2,3-butanedithiol and 3-chloro-2-butanone to give 2,3-dihydro-2,3,5,6-tetramethyl-1,4-dithiin, as a colorless liquid, b.p. 58°–60°0.02 mm, yield 60%. NMR 1.34 (6d), 1.87 (6s), 2.7–3.2 (2m) (CDCl$_3$). IR, 2950, 1600, 1435, 1365, 1150, 1060, 760, 680.

b. The procedure of Example 1(b) is followed to give 2,3-dihydro-2,3,5,6-tetramethyl-1,4-dithiin 1,1,4,4-tetroxide, as white crystals, m.p. 244°–246.5°, yield 46%. Anal. Calcd. for $C_8H_{14}O_4S_2$: C, 40.34; H, 5.92. Found: C, 40.39; H, 6.15. NMR 1.54 (6d), 2.17 (6s), 3.55–3.95 (2m) (CDCl$_3$). IR 2940, 1630, 1445, 1300, 1180, 1115, 1065, 750.

EXAMPLE 8 a. The procedure of Example 1(a) is followed using 2,3-butanedithiol and 1-chloro-2-butanone to give 2-ethyl-5,6-dihydro-5,6-dimethyl-1,4-dithiin as a colorless oil, b.p. 55°–58°/0.03-0.05 mm, yield 53%. NMR 1.08 (3t), 1.36 (6d), 2.18 (2q), 2.7–3.1 (2m), 5.78 (1s, broadened) (CDCl$_3$). IR 3000 (shoulder), 2955, 1570, 1440, 1365, 1110, 825, 705.

b. The procedure of Example 1(b) is followed to give 2-ethyl-5,6-dihydro-5,6-dimethyl-1,4-dithiin 1,1,4,4-tetroxide, as white crystals, m.p. 128°–132°. Yield 37%. NMR 1.23 (3t), 1.5 (6m), 2.66 (2, octet), 3.8 (2m), 6.51 (1s, broadened). IR 3020, 2940, 1620, 1315, 1275, 1115, 955, 740.

EXAMPLE 9 a. The procedure of Example 1(a) is followed using 2,3-butanedithiol and 2-chlorocyclohexanone to give 5,6,7,8-tetrahydro-2,3-dimethyl-1,4-benzodithian as a greenish oil, b.p. 90°–100°/0.07 mm. Yield 49%. NMR 1.34 (6d), 1.45–2.25 (8m), 2.7–3.1 (2m). IR 2900, 1610, 1435, 1365, 1320, 1115, 795, 690.

b. The procedure of Example 1(b) was followed to give 5,6,7,8-tetrahydro-2,3-dimethyl-1,4-benzodithian 1,1,4,4-tetroxide as white needles, m.p. 192°–195°, yield 57%. NRM 1.54 (6d), 1.6–2.1 (4m), 2.4–2.8 (4m), 3.81 (2m), (CDCl$_3$). IR 2940, 1450, 1420, 1310, 1260, 1130, 965, 740.

EXAMPLE 10 a. The procedure of Example 1(a) was followed using 1,2-propanedithiol and 2-bromo-3-pentanone to give a mixture of 2-ethyl-5,6-dihydro-3,5-dimethyl-1,4-dithiin and 2-ethyl-5,6-dihydro-3,6-dimethyl-1,4-dithiin as a greenish oil, b.p. 85°–90°/3 mm, yield 29%. IR 2905, 1615, 1410, 1215, 1155, 1060, 735, 705.

b. The procedure of Example 1(b) was followed to give a mixture of 2-ethyl-5,6-dihydro-3,5-dimethyl-1,4-dithiin 1,1,4,4-tetroxide and 2-ethyl-5,6-dihydro-3,6-dimethyl-1,4-dithiin 1,1,4,4-tetroxide as a clear, colorless, very viscous oil, yield 55%. NMR 1.01–1.38 (3t), 1.47–1.61 (3d), 2.16 (3s), 2.38–2.75 (2q), 3.3–4.05 (3m). (CDCl$_3$). IR 2970, 2930, 1620, 1310, 1170, 1110, 730, 690.

EXAMPLE 11 a. The procedure of Example 1(a) is followed, using chloroacetone and 1,2-propanedithiol to give a mixture of 2,3-dihydro-2,5-dimethyl-1,4-dithiin and 2,3-dihydro-2,6-dimethyl-1,4-dithiin as a colorless oil, bp 68°–77°/6 mm. NMR 1.39 (3d), 1.90 (3s), 2.5–3.65 (3m), 5.78 (1 quin). IR 3000, 2910, 1585, 1400, 1350, 1090, 810, 760.

b. The procedure of Example 1(b) is followed to give a mixture of 2,3-dihydro-2,5-dimethyl-1,4-dithiin 1,1,4,4-tetroxide and 2,3-dihydro-2,6-dimethyl-1,4-dithiin 1,1,4,4-tetroxide as long white needles, mp 160°–205°, Anal. Calcd. for $C_6H_{10}O_4S_2$: C, 34.29; H, 4.86. Found: C, 34.85; H, 4.81. NMR 1.51 (3d), 2.16–2.19 (3d), 3.6–4.2 (3m), 6.98 (1m) (CDCl$_3$-DMSO). IR 3010, 2970, 2920, 1620, 1400, 1300, 1120, 705.

EXAMPLE 12 a. The procedure of Example 1(a) is followed using 1-chloro-2-butanone and 1,2-propanedithiol to give a mixture of 2-ethyl-5,6-dihydro-5-methyl-1,4-dithiin and 2-ethyl-5,6-dihydro-6-methyl-1,4-dithiin as an oil, bp 79°–83°/1.3 mm, yield 30%. NMR 1.08 (3t), 1.40 (3d), 2.18 (2q), 2.5–3.6 (3m), 5.83 (1q) (CDCl$_3$).

b. The procedure of Example 1(b) is followed to give a mixture of 2-ethyl-5,6-dihydro-5-methyl-1,4-dithiin 1,1,4,4-tetroxide and 2-ethyl-5,6-dihydro-6-methyl-1,4-dithiin 1,1,4,4-tetroxide as long white needles, mp 141°–153° Yield 55%. Anal. Calcd. for $C_7H_{12}O_4S_2$: C, 37.50; H, 5.40. Found: C, 37.79, 37.59; H, 5.29, 5.23. NMR 1.18 (3t), 1.45 (3d), 2.52 (2q), 3.8–4.3 (3m), 7.28 (1m) (DMSO). IR 3010, 2980, 2920, 1630, 1400, 1295, 1120, 705.

EXAMPLE 13 a. The procedure of Example 1(a) is followed using chloroacetone and 1,2-butanedithiol to give a mixture of 2-ethyl-2,3-dihydro-5-methyl-1,4-dithiin and 2-ethyl-2,3-dihydro-6-methyl-1,4-dithiin as a greenish oil, bp 68–75% 0.8 mm.

b. The procedure of Example 1(b) is followed to give a mixture of 2-ethyl-2,3-dihydro-5-methyl-1,4-dithiin 1,1,4,4-tetroxide and 2-ethyl-2,3-dihydro-6-methyl-1,4-dithiin 1,1,4,4-tetroxide as white crystals, mp 111°–142°. NMR 1.17 (3t), 1.4–2.4. (2q), 2.20 (3m), 3.80 (3m), 6.85 (1m) (CDCl$_3$). IR 3025, 2980, 2930, 1625, 1405, 1305, 1120 750.

EXAMPLE 14 a. The procedure of Example 1(a) is repeated, using 1,2-butanedithiol and 1-chloro-2-butanone to give a mixture of 2,5-diethyl-2,3-dihydro-1,4-dithiin and 2,6-diethyl-2,3-dihydro-1,4-dithiin as a slightly greenish oil, bp 77°–78°/0.6. NMR 1.01 (3t), 1.4–2.6 (2m), 1.32 (3t), 1.44 (2q), 2.6–3.4 (3m), 5.78 (1m), yield 69%. IR 3000, 2910, 1585, 1410, 1220, 1095, 810, 755.

b. The procedure of Example 1(b) is repeated, giving a mixture of 2,5-diethyl-2,3-dihydro-1,4-dithiin 1,1,4,4-tetroxide and 2,6-diethyl-2,3-dihydro-1,4-dithiin 1,1,4,4-tetroxide as white needles, mp 99°–136°, yield 65%. Anal. Calcd. for $C_8H_{14}O_4S_2$: C, 40.34; H 5.92. Found: C, 39.90, 40.31; H, 5.84, 5.90. NMR 1.17 (3t), 1.22 (3t), 1.4–2.6 (2m), 2.63 (2a), 3.4–4.1 (3m), 6.47 (1m), (CDCl$_3$). IR 3010, 2970, 1620, 1395, 1300, 1120, 760, 680.

EXAMPLE 15 a. The procedure of Example 1(a) was followed using 1,2-cyclohexanedithiol and 3-chloro-2-butanone to give 4a,5,6,7,8,8a-hexahydro-2,3-dimethyl-1,4-benzodithiin as a colorless oil, bp 100°–102°/0.2 mm. Yield 78%. NMR 1.07–2.2 (8m), 1.85 (6s), 2.9–3.2 (2m). IR 2924, 2850, 1615, 1440, 1335, 1275, 1180, 985.

b. The procedure of Example 1(b) was followed to give 4a,5,6,7,8,8a-hexahydro-2,3-dimethyl-1,4-benzodithiin 1,1,4,4-tetroxide as white needles. Anal. Calcd. for $C_{10}H_{16}O_4S_2$: C, 45.45; H, 6.10. Found: C, 45.65; H, 6.29.

EXAMPLE 16 a. To a boiling solution of 1,2-cyclohexanedithiol (44.4 g.) in benzene (250 ml) with a trace of p-toluenesulfonic acid was added 1-chloro-2-butanone (31.8 g.) in benzene over 2 hrs. The solution was heated under reflux for 35 hours with water removal by means of a Dean-Stark trap. The reaction mixture was washed with cold aqueous sodium hydroxide and water, dried and reduced to an oil under vacuum. The crude 2-ethyl-4a, 5,6,7,8,8a-hexahydro-1,4-benzodithiin was distilled at high vacuum to give a colorless oil mainly boiling at 100°/0.1 mm. Yield 63%. NMR 1.09 (3t), 0.9–2.4 (8m), 2.19 (2q), 2.8–3.15 (2m), 5.80 (1t) CDCl$_3$). IR 3000, 2930, 1585, 1335, 1275, 1125, 875, 840.

b. The procedure of Example 1(b) is followed to give 2-ethyl-4a,5,6,7,8,8a-hexahydro-1,4-benzodithiin 1,1,4,4-tetroxide as white needles, mp 140°–142°. Anal. Calcd. for $C_{10}H_{16}O_4S_2$: C, 45.45; H 6.10. Found: C, 45.82; H, 6.13. NMR 1.22 (3t), 1–2.6 (8m), 2.67 (2q), 3.6–3.9 (4d), 6.52 (1t) CDCl$_3$). Yield 64%. IR 3020, 2940, 1630, 1300 1260, 1120, 760, 680.

EXAMPLE 17 a. The procedure of Example 1(a) is followed using 2-chlorocyclohexanone and ethanedithiol to give 5,6,7,8-tetrahydro-1,4-benzodithian as a greenish oil, bp 90°/0.5 mm, yield 45% NMR 3.18 (4s), ring protons, IR 2920, 1610, 1410, 1325, 1280, 1125, 1025, 785.

b. The procedure of Example 1(b) is followed to give 5,6,7,8-tetrahydro-1,4-benzodithian 1,1,4,4-tetroxide as large translucent crystals, mp 172°–175°, yield 41%. Anal. Calcd. for $C_8H_{12}O_4S_2$: C, 40.68; H, 5.12. Found: C, 40.77; H, 5.05. IR, 2990, 2935, 1630, 1400, 1300, 1125, 880, 750.

Example 18

To illustrate effectiveness of the described dithiin tetroxides as preemergence herbidides, 600 mg chemical is dissolved in 10 ml organic solvent (e.g., acetone) to which 30 mg conventional emulsifying agent (e.g. isooctylpolyethoxyethanol "Triton X100" [trademark]) is added. The solution is diluted to 100 ml with distilled water. Twenty milliliters of this 6000 ppm solution is diluted to 500 ppm with distilled water. The chemical is applied at the rate of 10 lb./A (pounds per acre) by drenching 23 ml of the 500 ppm solution on the surface of soil in 4½-inch plastic pots which had been planted with the following weeds: rough pigweed (*Amaranthus retroflexus* L.), purslane (*Portulaca oleracea* L.), tall morningglory (*Ipomea purpurea* L. Roth), crabgrass (*Digitaria ischaemum* (Schreb.) Muhl.), Barnyardgrass (*Echinochloa crusgalli* (L) Beaur.), giant foxtail (*Setaria faberi* Herrm.) and southern nutsedge (*Cyperus rotundus* L.). The percent control of the weeds compared to untreated checks is determined two weeks after treatment. TABLE I shows the results with the preemergence herbicides of the invention prepared in accordance with the above examples.

TABLE I

Dithiin Tetroxide Preemergence Herbicides
Percent Control of Weeds at Rate of 10 Lb/A

| Chem. of Ex. | Pigweed | Purslane | Tall M. glory | B-yard grass | Crabgrass | Foxtail | Nutsedge |
|---|---|---|---|---|---|---|---|
| 1  | 100 | 100 | 100 | 100 | 100 | 100 | 50 |
| 2  | 100 | 100 | 0   | 60  | 100 | 100 | 0 |
| 3  | 100 | 100 | 50  | 100 | 100 | 100 | 0 |
| 6  | 100 | 100 | 90  | 100 | 100 | 100 | 0 |
| 17 | 100 | 100 | 95  | 98  | 100 | 100 | 0 |
| 4  | 100 | 100 | 0   | 80  | 50  | 90  | 0 |
| 15 | 100 | 100 | 95  | 65  | 100 | 100 | 0 |
| 16 | 100 | 100 | 0   | 35  | 30  | 0   | 0 |
| 13 | 100 | 100 | 60  | 15  | 0   | 25  | 0 |
| 14 | 0   | 100 | 0   | 0   | 50  | 50  | 0 |
| 5  | 30  | 0   | 0   | 75  | 85  | 75  | 0 |
| 11 | 100 | 100 | 0   | 50  | 25  | 50  | 0 |

TABLE I-continued

Dithiin Tetroxide Preemergence Herbicides
Percent Control of Weeds at Rate of 10 Lb/A

| Chem. of Ex. | Pig-weed | Purs-lane | Tall M. glory | B-yard grass | Crab-grass | Fox-tail | Nut-sedge |
|---|---|---|---|---|---|---|---|
| 12 | 100 | 100 | 0 | 85 | 100 | 100 | 0 |
| 7 | 100 | 100 | 73 | 90 | 95 | 95 | 0 |
| 8 | 100 | 100 | 25 | 90 | 95 | 100 | 0 |
| 9 | 90 | 90 | 0 | 0 | 90 | 50 | 0 |
| 10 | 100 | 100 | 82 | 98 | 100 | 100 | 0 |

EXAMPLE 19

To illustrate effectiveness of the described dithiin tetroxides as postemergence herbicides, the 6000 ppm solution described under Example 18 is atomized with a conventional DeVilbiss sprayer, wetting the foliage to the drip point. The weeds, which are the same species as described under Example 18, are treated six days after emergence. The percent control is evaluated two weeks after treatment. TABLE II shows the results with the postemergence herbicides of the invention.

TABLE II

Dithiin Tetroxide Postemergence Herbicides
Percent Control of Weeds With 6000 PPM Solution

| Chem. of Ex. | Pig-weed | Purs-lane | Tall M. glory | Barn-yard grass | Crab-grass | Giant Fox-tail | Nut-sedge |
|---|---|---|---|---|---|---|---|
| 1 | 90 | 90 | 90 | 90 | 90 | 90 | 25 |
| 2 | 100 | 70 | 80 | 80 | 80 | 100 | 0 |
| 3 | 100 | 100 | 100 | 100 | 90 | 100 | 0 |
| 6 | 98 | 100 | 100 | 98 | 95 | 85 | 10 |
| 7 | 100 | 100 | 10 | 75 | 25 | 15 | 0 |
| 8 | 100 | 90 | 0 | 90 | 15 | 10 | 0 |
| 9 | 100 | 100 | 0 | 35 | 30 | 15 | 0 |
| 10 | 90 | 90 | 90 | 90 | 80 | 80 | 0 | taining 25 mg conventional emulsifying agent and this solution diluted to 300 ml with distilled water. The chemical is applied at the rate of 2 lbs/A by drenching the surface of soil containing weed and crop seeds in 6-inch plastic pots with 80 ml of the 50 ppm solution. The percent weed control and crop injury are evaluated two weeks after emergence of the crops. TABLE III illustrates the usefulness of these chemicals as selective preemergence herbicides.

TABLE III

Dithiin Tetroxide Selective Preemergence Herbicides
Percent Weed Control and Crop Injury at Rate of 2Lb/A

| Chem. of Ex. | Pig-weed | Purs-lane | Tall Morn. Glory | Barn-yard grass | Crab-grass | Giant Fox-Tail | Corn | Rice |
|---|---|---|---|---|---|---|---|---|
| 1 | 100 | 100 | 100 | 100 | 100 | 100 | 40 | 60 |
| 17 | 100 | 100 | 50 | 60 | 50 | 60 | 0 | 0 |
| 3 | 100 | 100 | 80 | 100 | 95 | 100 | 10 | 30 |
| 6 | 100 | 100 | 75 | 90 | 90 | 100 | 0 | 0 |

EXAMPLE 20

To illustrate activity as an algicide and an aquatic herbicide, 5L of a 1000 ppm solution of the chemical of Example 1, namely, 2,3-dihydro-5,6-dimethyl-1,4-dithiin 1,1,4,4-tetroxide was poured into a plastic pot containing green algae (Spirogyra) filaments and water-hyacinth (*Eichornia crassipes* (Mart.) Solms) plants. After ten days, containers of untreated water supported an algae growth and live water hyacinth plants. However, the plants growing in the 1000 ppm solution died within 10 days.

EXAMPLE 21

Selectivity of a herbicide is desirable since it allows control of weeds growing among desirable crop plants. To illustrate the usefulness of the dithiin tetroxides of the invention as selective preemergence herbicides, 15 mg chemical are dissolved in 5 ml organic solvent con-

EXAMPLE 22

To illustrate the effectiveness of dithiin tetroxides of the invention as harvest aid chemicals, specifically as desiccants or defoliants for cotton, 600 mg chemical is dissolved in either distilled water or 5 ml organic solvent (e.g., acetone) to which 30 mg conventional emulsifying agent (e.g., isooctyl polyethoxyethanol, "Triton X100" [trademark]) is added. Cotton, *Gossypium hirsutum* (L), at the first true leaf stage is sprayed with the formulated chemical by atomizing the chemical with a conventional Devilbiss sprayer, wetting the plant to the drip point. Two weeks after the spraying, the plants are examined and an estimate of the percentage area of leaf tissue killed is made (the result is reported as percent desiccation, which is a manifestation of phytotoxicity, in TABLE IV) or the percentage of leaves which have dropped is estimated (the result is reported as percent defoliation in TABLE IV). The chemicals shown to produce desiccation in TABLE IV will, at lower rates, produce defoliation, which in many cases is more desirable.

TABLE IV

Dithiin Tetroxide Cotton Desiccanats/Defoliants

| Chem. of Ex. | Percent Desiccation/Defoliation at 6000 PPM |
|---|---|
| 1 | 100 Desiccation |
| 2 | 85 Desiccation |
| 3 | 100 Desiccation |
| 6 | 100 Desiccation |
| 5 | 100 Desiccation |
| 4 | 100 Defoliation |
| 7 | 100 Desiccation |
| 8 | 100 Desiccation |
| 9 | 50 Desiccation |
| 10 | 85 Desiccation |

EXAMPLE 23

Defoliation response on cotton is further demonstrated in this example, together with the important property of regrowth inhibition. Four hundred and eighty mgs chemical is dissolved in either water or 5 ml toluene, mixed homogeneously, and this solution diluted to 120 ml with water. Mature cotton plants with 4 to 5 well developed bolls are sprayed to the drip point with the desired chemical. Ten days after application of the chemical the percent defoliation is estimated and thirty days after application the plants are inspected for regrowth, with the results shown in TABLE V, wherein the percent regrowth control is estimated by comparison with an untreated check plant.

TABLE V

Mature Cotton Defoliant and Regrowth Test with Dithiin tetroxides

| Chem. of Ex. | Rate, ppm | % Defoliation | % Regrowth Control |
|---|---|---|---|
| 1 | 3000 | 100 | 100 |
|   | 1500 | 100 | 96.7 |
| 6 | 3000 | 100 | 96.7 |
|   | 1500 | 83.3 | 96.7 |
| 3 | 4000 | 100 |   |
|   | 2000 | 100 |   |

EXAMPLE 24

This example illustrates the effectiveness of 2,3-dihydro-5,6-dimethyl-1,4-dithiin 1,1,4,4-tetroxide as a harvest aid chemical on potatoes. Four g. this chemical was dissolved in 1000 ml water (50° C) to give a 4000 ppm solution, and one-half percent of a surfactant (e.g., condensation product of trimethylnonanol with 6 to 13 moles of ethylene oxide, "Adjuvan T" [trademark]) was added. A diluted 1000 ppm solution was also prepared. The solutions were sprayed to the point of run off on 20 feet of Green Mountain White potato vines. The vines were actively growing at application time. Ten days after the applications of spray solutions, the leaf defoliation, as well as vine kill, were 100%, with both solutions.

EXAMPLE 25

This example illustrates citrus abscission. The following materials were mixed to make a dry powder:

|   | Mgs |
|---|---|
| 2,3-Dihydro-5,6-dimethyl-1,4- |   |
| dithiin 1,1,4,4-tetroxide | 200 |
| Surfactants: |   |
| Alkaryl polyether alcohol (=Triton X120" [trademark]) | 4 |
| Sodium N-methyl-N-palmitoyl laurate ("Igepon TN-74" [trademark]) | 4 |
| Polymerized sodium salts of alkyl naphthalene sulfonic acid ("Daxad-11" [trademark]) | 8 |
| Powders: |   |
| Kaolin clay ("Dixie Clay" [trademark]) | 56 |
| Silica ("Hi Sil 233" [trademark]) | 128 |
|   | 400 |

The foregoing was suspended in 1000 ml water. This is equivalent to 200 ppm active chemical. Dosages of 100, 50 and 25 ppm were made from the 200 ppm stock solution. A single citrus (orange) branch with 30 fruits was marked and sprayed to runoff with each dilution. Seven days later degree of abscission was measured by recording the average number of pull pounds required to remove fruit from the branch. The data in TABLE VI illustrate the chemical abscission properties, expressed as the average pull from 10 fruit.

TABLE VI

Abscission of Citrus with 2,3-Dihydro-5,6-dimethyl-1,4-dithiin 1,1,4,4-tetroxide

| Rate PPM | Average Pull Pounds |
|---|---|
| 200 | 10.3 |
| 100 | 12.6 |
| 50 | 17.9 |
| 25 | 20.6 |
| 0 | 22.0 |

We claim:

1. A method of controlling weeds comprising applying to a locus at which it is desired to control said weeds, in a herbicidally effective amount, a 2,3-dihydro-1,4-dithiin 1,1,4,4-tetroxide of the formula:

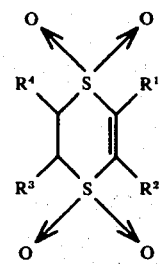

wherein $R^1$, $R^2$, $R^3$ and $R^4$ are selected from the group consisting of hydrogen and lower alkyl having one to two carbon atoms, not more than two of the R's being hydrogen, or an adjacent pair of R's are connected together in the form of a chain of three to four methylene groups.

2. A method as in claim 1, wherein the R's have sets of values as follows:

| $R^1$ | $R^2$ | $R^3$ | $R^4$ |
|---|---|---|---|
| $CH_3$ | $CH_3$ | H | H |
| $C_2H_5$ | $CH_3$ | H | H |
| $CH_3$ | $CH_3$ | H | $CH_3$ |
|   | —$(CH_2)_4$— | $CH_3$ | H |
|   | —$(CH_2)_3$— | $CH_3$ | H |

-continued

| R¹ | R² | R³ | R⁴ |
|---|---|---|---|
| CH₃ |  | CH₃ | C₂H₅ | H |
| CH₃ |  | CH₃ | CH₃ | CH₃ |
| C₂H₅ |  | H | CH₃ | CH₃ |
| —(CH₂)₄— |  | CH₃ | CH₃ |
| C₂H₅ |  | CH₃ | CH₃ | H |
| C₂H₅ |  | CH₃ | H | CH₃ |
| CH₃ |  | H | H | CH₃ |
| H |  | CH₃ | H | CH₃ |
| C₂H₅ |  | H | CH₃ | H |
| C₂H₅ |  | H | H | CH₃ |
| CH₃ |  | H | H | C₂H₅ |
| CH₃ |  | H | C₂H₅ | H |
| C₂H₅ |  | H | H | C₂H₅ |
| C₂H₅ |  | H | C₂H₅ | H |
| CH₃ |  | CH₃ | —(CH₂)₄— |
| C₂H₅ |  | H | —(CH₂)₄— |
| —(CH₂)₄— |  | H | H |

3. A method as in claim 2 in which the control of weeds is preemergence control of weeds, and the chemical of the said formula is applied to soil in which preemergence control of weeds is desired, in amount sufficient to effect preemergence herbicidal action.

4. A method as in claim 2 in which the control of weeds is postemergence control of weeds, and the chemical of the said formula is applied to plants with which postemergence control of weeds is desired, in amount sufficient to effect postemergence herbicidal action on said weeds.

5. A method as in claim 2 in which the said chemical is applied in admixture with a surface active agent.

6. A method as in claim 2 in which the chemical is 2,3-dihydro-5,6-dimethyl-1,4-dithiin 1,1,4,4-tetroxide.

7. A method as in claim 2 in which the chemical is 2-ethyl-5,6-dihydro-3-methyl-1,4-dithiin 1,1,4,4-tetroxide.

8. A method as in claim 2 in which the chemical is 2,3-dihydro-2,5,6-trimethyl-1,4-dithiin 1,1,4,4-tetroxide.

9. A method as in claim 2 in which the chemical is 5,6,7,8-tetrahydro-2-methyl-1,4-benzodithian 1,1,4,4-tetroxide.

10. A method as in claim 2 in which the chemical is 2,3,6,7-tetrahydro-2-methyl-5H-cyclopenta-1,4-dithiin-1,1,4,4-tetroxide.

11. A method as in claim 2 in which the chemical is 2-ethyl-2,3-dihydro-5,6-dimethyl-1,4-dithiin 1,1,4,4-tetroxide.

12. A method as in claim 2 in which the chemical is 2,3-dihydro-2,3,5,6-tetramethyl-1,4-dithiin 1,1,4,4-tetroxide.

13. A method as in claim 2 in which the chemical is 2-ethyl-5,6-dihydro-5,6-dimethyl-1,4-dithiin 1,1,4,4-tetroxide.

14. A method as in claim 2 in which the chemical is 5,6,7,8-tetrahydro-2,3-dimethyl-1,4-benzodithian 1,1,4,4-tetroxide.

15. A method as in claim 2 in which the chemical is 2-ethyl-5,6-dihydro-3,5-dimethyl-1,4-dithiin, 1,1,4,4-tetroxide.

16. A method as in claim 2 in which the chemical is 2-ethyl-5,6-dihydro-3,6-dimethyl-1,4-dithiin 1,1,4,4-tetroxide.

17. A method as in claim 2 in which the chemical is 2,3-dihydro-2,5-dimethyl-1,4-dithiin 1,1,4,4-tetroxide.

18. A method as in claim 2 in which the chemical is 2,3-dihydro-2,6-dimethyl-1,4-dithiin 1,1,4,4-tetroxide.

19. A method as in claim 2 in which the chemical is 2-ethyl-5,6-dihydro-5-methyl-1,4-dithiin 1,1,4,4-tetroxide.

20. A method as in claim 2 in which the chemical is 2-ethyl-5,6-dihydro-6-methyl-1,4-dithiin 1,1,4,4-tetroxide.

21. A method as in claim 2 in which the chemical is 2-ethyl-2,3-dihydro-5-methyl-1,4-dithiin 1,1,4,4-tetroxide.

22. A method as in claim 2 in which the chemical is 2-ethyl-2,3-dihydro-6-methyl-1,4-dithiin 1,1,4,4-tetroxide.

23. A method as in claim 2 in which the chemical is 2,5-diethyl-2,3-dihydro-1,4-dithiin 1,1,4,4-tetroxide.

24. A method as in claim 2 in which the chemical is 2,6-diethyl-2,3-dihydro-1,4-dithiin 1,1,4,4-tetroxide.

25. A method as in claim 2 in which the chemical is 4a,5,6,7,8,8a-hexahydro-2,3-dimethyl-1,4-benzodithiin 1,1,4,4-tetroxide.

26. A method as in claim 2 in which the chemical is 2-ethyl-4a,5,6,7,8,8a-hexahydro-1,4-benzodithiin 1,1,4,4-tetroxide.

27. A method as in claim 2 in which the chemical is 5,6,7,8-tetrahydro-1,4-benzodithian 1,1,4,4-tetroxide.

* * * * *